(12) United States Patent
Limaye et al.

(10) Patent No.: US 10,130,769 B2
(45) Date of Patent: Nov. 20, 2018

(54) SYRINGE WITH VISUALLY CODED NEEDLE HUB

(71) Applicant: Becton, Dickinson and Company, Franklin Lakes, NJ (US)

(72) Inventors: Amit Limaye, Wayne, NJ (US); Claire Levine, Wayne, NJ (US); Matthew deFreese, Holdrege, NE (US); Rick Reiners, Holdrege, NE (US); Edward Rosen, Morristown, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 313 days.

(21) Appl. No.: 15/012,687

(22) Filed: Feb. 1, 2016

(65) Prior Publication Data

US 2016/0158449 A1 Jun. 9, 2016

Related U.S. Application Data

(62) Division of application No. 13/442,592, filed on Apr. 9, 2012, now Pat. No. 9,272,099.

(51) Int. Cl.
*A61M 5/46* (2006.01)
*A61M 5/31* (2006.01)
(Continued)

(52) U.S. Cl.
CPC .............. *A61M 5/31* (2013.01); *A61J 1/1406* (2013.01); *A61M 5/3129* (2013.01);
(Continued)

(58) Field of Classification Search
CPC .... A61M 5/31; A61M 5/3129; A61M 5/3293; A61M 2005/3126; A61M 2205/6009;
(Continued)

(56) References Cited

U.S. PATENT DOCUMENTS

| 4,439,187 A | 3/1984 | Butterfield |
| 4,997,423 A | 3/1991 | Okuda et al. |

(Continued)

FOREIGN PATENT DOCUMENTS

| CN | 200980872 Y | 11/2007 |
| EP | 1935444 A1 | 6/2008 |

(Continued)

OTHER PUBLICATIONS

BD Medical Systems, BD Saf-T-Intima IV Catheters, BD Angiocath IV Catheters, BD Autoguard Shielded IV Catheters, BD IV Catheter Family, Brochure, Mar. 2006, pp. 1 and 2.
(Continued)

*Primary Examiner* — Ryan J Walters
(74) *Attorney, Agent, or Firm* — Dickinson Wright PLLC (57) ABSTRACT

A medication delivery device included molded cylindrical barrel having visual marks on the surface of the barrel in the axial direction, a plunger seals the distal opening of the cylindrical barrel, a molded needle hub disposed in the proximal opening of the cylindrical barrel for sealing the needle hub to the barrel. A needle is disposed in the needle hub for communicating liquids by operation of the plunger in the axial direction. The circumferential surface on the flange of the needle hub comprises a colored mark that corresponds to a characteristic of the medication delivery device or its contents.

9 Claims, 7 Drawing Sheets

(51) Int. Cl.
*A61J 1/14* (2006.01)
*B65B 63/00* (2006.01)
*A61M 5/00* (2006.01)
*A61J 1/06* (2006.01)
*A61M 5/32* (2006.01)
*A61M 5/34* (2006.01)

(52) U.S. Cl.
CPC ......... *A61M 5/3293* (2013.01); *B65B 63/005* (2013.01); *A61J 1/065* (2013.01); *A61J 2205/20* (2013.01); *A61M 5/002* (2013.01); *A61M 5/3202* (2013.01); *A61M 5/348* (2013.01); *A61M 2005/3125* (2013.01); *A61M 2005/3126* (2013.01); *A61M 2205/584* (2013.01); *A61M 2205/6009* (2013.01); *A61M 2205/6081* (2013.01); *A61M 2207/00* (2013.01)

(58) Field of Classification Search
CPC .... A61M 2205/584; A61M 2005/3125; A61M 2207/00; A61M 5/348; A61M 5/002; A61M 5/3202; B65B 63/005; A61J 1/1406; A61J 2205/20; A61J 1/065
See application file for complete search history.

(56) References Cited

U.S. PATENT DOCUMENTS

| | | | |
|---|---|---|---|
| 5,015,241 | A | 5/1991 | Feimer |
| 5,037,393 | A | 8/1991 | Ellgass |
| 5,047,017 | A | 9/1991 | Koska |
| 5,083,921 | A | 1/1992 | Dragan |
| 5,188,616 | A | 2/1993 | Nadal |
| 5,328,466 | A | 7/1994 | Demark |
| 5,356,406 | A | 10/1994 | Schraga |
| 5,669,887 | A | 9/1997 | Cooper |
| 5,730,292 | A | 3/1998 | Jones |
| 5,792,117 | A | 8/1998 | Brown |
| 5,814,017 | A | 9/1998 | Kashmer |
| D419,671 | S | 1/2000 | Jansen |
| 6,132,416 | A | 10/2000 | Broselow |
| 6,267,749 | B1 | 7/2001 | Miklos et al. |
| D447,797 | S | 9/2001 | Odell et al. |
| 6,290,678 | B1 | 9/2001 | Aydelotte et al. |
| D457,954 | S | 5/2002 | Wallace et al. |
| 6,494,863 | B1 | 12/2002 | Shaw et al. |
| D480,477 | S | 10/2003 | Bush et al. |
| D493,526 | S | 7/2004 | Hwang |
| 7,793,846 | B2 | 9/2010 | Jones |
| D638,122 | S | 5/2011 | Kosinski et al. |
| D638,123 | S | 5/2011 | Kosinski et al. |
| D638,537 | S | 5/2011 | Virr et al. |
| 8,002,756 | B2 | 8/2011 | Walters et al. |
| D649,242 | S | 11/2011 | Kosinski et al. |
| D650,903 | S | 12/2011 | Kosinski et al. |
| 8,361,055 | B2 | 1/2013 | Tucker |
| 2002/0185406 | A1 | 12/2002 | Massengale et al. |
| 2004/0186437 | A1 | 9/2004 | Frenette et al. |
| 2005/0119622 | A1 | 6/2005 | Temple |
| 2005/0148941 | A1 | 7/2005 | Farrar et al. |
| 2006/0084925 | A1 | 4/2006 | Ramsahoye |
| 2006/0282045 | A1 | 12/2006 | Wilkinson et al. |
| 2007/0142786 | A1 | 6/2007 | Lampropoulos et al. |
| 2007/0208311 | A1 | 9/2007 | Farrar et al. |
| 2008/0045929 | A1 | 2/2008 | Birnbach |
| 2009/0259179 | A1 | 10/2009 | Hillios et al. |
| 2010/0130961 | A1 | 5/2010 | Tucker |
| 2010/0217206 | A1 | 8/2010 | Lum et al. |
| 2011/0225790 | A1 | 9/2011 | Farrar et al. |
| 2013/0144255 | A1 | 6/2013 | Cohn |

FOREIGN PATENT DOCUMENTS

| | | |
|---|---|---|
| GB | 2458126 A | 9/2009 |
| JP | U-S49-080094 | 7/1974 |
| JP | U-S51-149991 | 11/1976 |
| JP | 2005270579 A | 10/2005 |
| JP | 2007-130436 | 5/2007 |
| JP | 2007-517594 A | 7/2007 |
| WO | WO-03037411 A1 | 5/2003 |
| WO | WO-2004012788 A2 | 2/2004 |
| WO | WO-2011138316 A1 | 11/2011 |
| WO | WO-2012020089 A1 | 2/2012 |

OTHER PUBLICATIONS

BD Medical, BD Saf-T-Intima IV Catheters, BD Angiocath IV Catheters, Mar. 2006, 1 page.
Becton, Dickinson and Company, BD Autoguard Shielded IV Catheters, BD IV Catheter Family, 1 page.
Becton, Dickinson and Company, BD Insulin Syringe with BD Ultra-Fine Short Needle, 1 page, http://www.bd.com/us/diabetes/page.aspx?=cat7002&id=7407, Accessed on Jan. 25, 2012.
Becton, Dickinson and Company, BD Insulin Syringe with the BD Micro-Fine Needle, 1 page, http://www.bd.com/us/diabetes/page.aspx?=cat7002&id=7408, Accessed on Jan. 25, 2012.
Becton, Dickinson and Company, BD Insulin Syringe with the BD Ultra-Fine Needle, 1 page, http://www.bd.com/us/diabetes/page.aspx?=cat7002&id=7406, Accessed on Jan. 25, 2012.
Becton, Dickinson and Company, BD Pharmacy Products, Catalog, Dec. 2006, 10 pages.
Becton, Dickinson and Company, BD Safety-Lok Syringe, Quick Reference Card, Feb. 2001, 2 pages.
Becton, Dickinson and Company, Discover How BD Insulin Syringes and Pen Needles Can Help Ease Your Diabetes Injection Experience, 2011, 6 Pages.
Becton, Dickinson and Company, Hypodermic Product Catalog, Catalog, Apr. 2006, 9 Pages.
Becton, Dickinson and Company, New Safety Needle Hub Color Chart, 2001, 1 page.
Wikipedia, Syringe, 7 pages, http://en.wikipedia.org/wiki/Syringe#cite_note-3, Accessed on Feb. 2, 2012.

SYRINGE WITH VISUALLY CODED NEEDLE HUB

RELATED APPLICATIONS

This application is a divisional of currently pending U.S. patent application Ser. No. 13/442,592, which is hereby incorporated by reference in its entirety, and which was filed on Apr. 9, 2012.

FIELD OF THE INVENTION

The present invention relates generally to syringes, and more particularly, to syringes with visually coded needle hubs to designate needle gauge, needle length, syringe type, or the like.

BACKGROUND OF THE INVENTION

One mode of insulin therapy for diabetes is injection of insulin via disposable syringes. Generally, a user removes a safety cap disposed over the needle on the syringe, pierces a cover of an insulin container with the needle, and withdraws a predetermined amount of insulin to prepare the insulin for injection. The user then pierces his or her skin with the needle and injects the insulin. After injecting the insulin, the syringe is discarded.

Conventional disposable syringes generally include a molded cylindrical barrel, a needle hub fastened to the barrel, and a needle disposed in the needle hub to communicate liquids disposed in the barrel by operation of a plunger. Syringes are marked along the barrel with visual indicators of the volume of liquid disposed within the barrel to allow a user to withdraw and inject the correct volume of medication. Conventional molded needle hubs are not separately marked after assembly, making it difficult to ascertain the properties of the needle.

In insulin treatment, there are different insulin concentrations available to users. To accommodate the different concentrations of insulin, the markings on the syringe barrel may correspond to units of insulin of a particular insulin concentration. Therefore, if two co-habitating insulin users have different insulin requirements, it may be possible for one of the users to inadvertently use an incorrect syringe and inject an incorrect insulin dosage.

SUMMARY OF EMBODIMENTS OF THE INVENTION

An object of embodiments of the present invention is to substantially address the above and other concerns, and to provide improved insulin injection devices. These and other objects are substantially achieved by providing a molded cylindrical barrel having visual marks on the surface of the barrel in the axial direction, a plunger having a stopper attached to an end of the plunger to seal the distal opening of the cylindrical barrel, and a molded needle hub disposed in the proximal opening of the cylindrical barrel for sealing the cylindrical barrel.

The needle hub comprises a flange having a circumferential surface that comprises a visually coded mark such as a color. The mark corresponds to a characteristic of the syringe such as needle gauge, needle length, syringe type, medication, or units of medication associated with the visual marks on the surface of the barrel. The circumferential surface of the flange may radially extend beyond the surface of the barrel to allow easy identification of the syringe and its associated characteristics.

In the exemplary embodiments disclosed herein, a generic needle hub may be manufactured without a needle and specific syringes may be made from the generic needle hub based on production requirements to thereby facilitate manufacturing. In yet other embodiments, a needle is fixed to the needle hub and marked with a visual mark on the needle hub's surface to identify the characteristics of needle to facilitate manufacturing.

BRIEF DESCRIPTION OF THE DRAWINGS

The various objects, advantages and novel features of the exemplary embodiments of the present invention will be more readily appreciated from the following detailed description when read in conjunction with the appended drawings, in which.

DETAILED DESCRIPTION OF EXEMPLARY EMBODIMENTS

Figure 1:
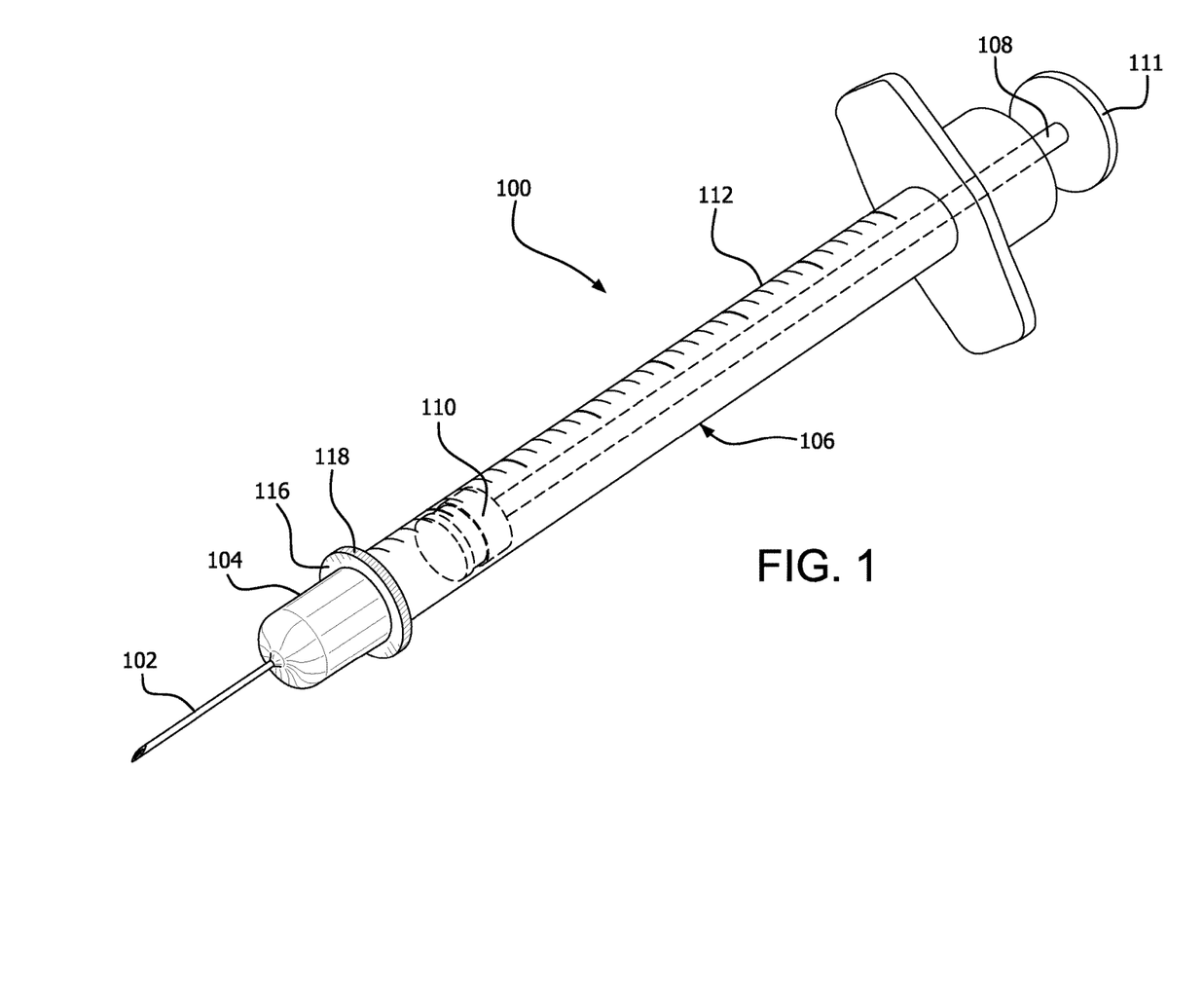
FIG. 1 is a perspective view of a syringe in accordance with an exemplary embodiment of the present invention.

FIG. 1 illustrates an exemplary embodiment of a medication delivery device such as a plastic disposable syringe 100 having a needle 102 at its proximal end and disposed in a molded needle hub 104. As will be described below, the needle hub 104 is fastened to an open proximal end of a molded cylindrical barrel 106 and a plunger 108 is disposed at an open distal end of the cylindrical barrel 106. The plunger 108 includes a stopper 110 that is configured to seal the distal end of the barrel 106. The stopper 110 may be integral to the plunger 108. A distal end of the plunger 108 includes a thumb press 111 to provide an interface for a user to move the plunger 108 in the axial direction of the barrel 106. By pulling or depressing the plunger, a user is able to transfer fluids to and from the syringe 100 at its proximal end via the needle 102. The outer surface of the barrel 106 includes visual markings 112 to indicate either the volume or the dosage of the liquid disposed within the syringe 100. For instance, the markings 112 may be associated with a particular insulin concentration so that the user can determine how many units of insulin to withdraw from a corresponding insulin container for injection. That is, the markings 112 may be in insulin units that correspond to a particular insulin concentration. The markings 112 may also be associated with a volume of liquid or any other suitable visual displays associated with the liquid disposed in the syringe 100.

Figure 2:
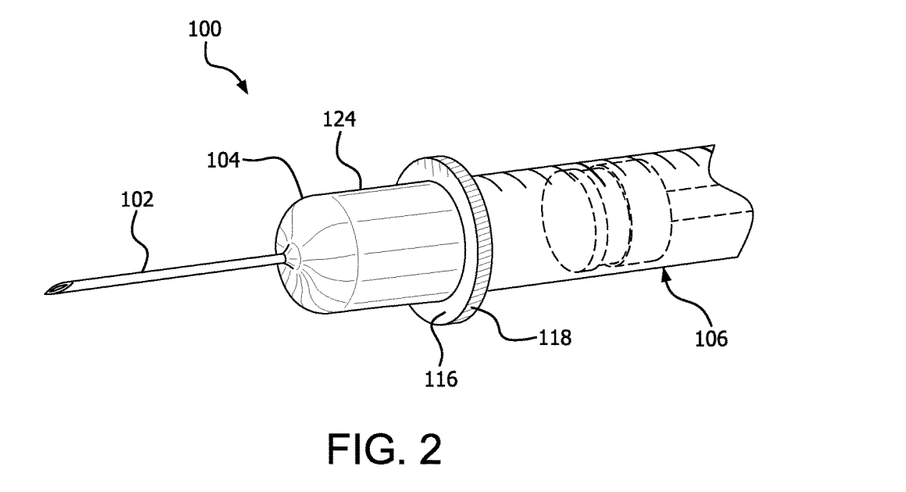
FIG. 2 is an partial view of the proximal end of the syringe of FIG. 1 showing the needle hub in more detail.
Figure 3:
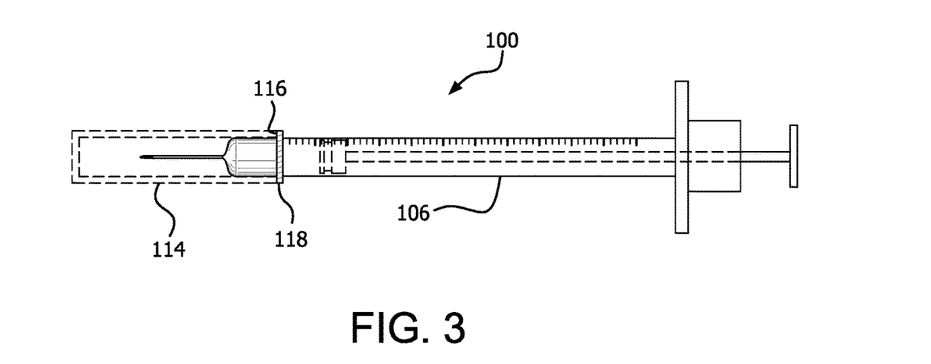
FIG. 3 is a side view of a fully assembled syringe of FIG. 1 with a needle safety shield disposed over the needle.
Figure 4:
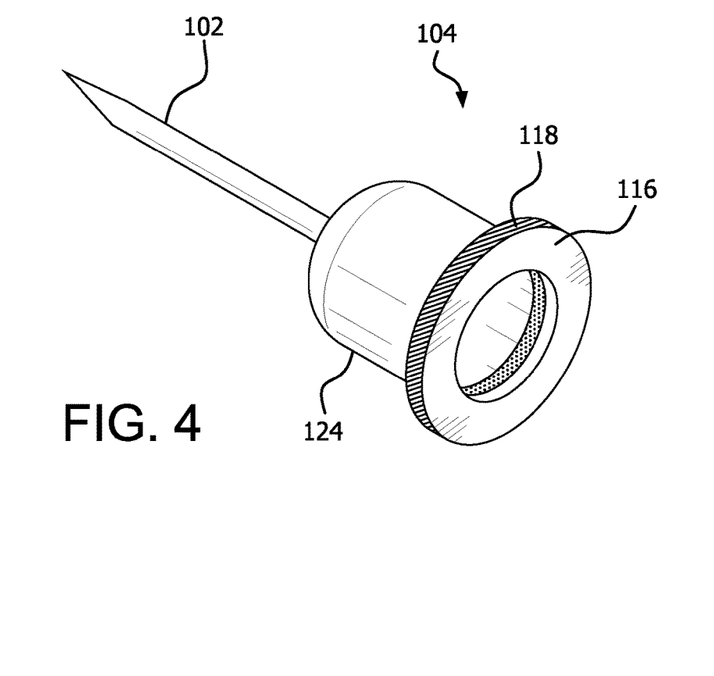
FIG. 4 is a perspective view of the needle hub in accordance with an exemplary embodiment of the present invention.

FIGS. 2-4 illustrate the syringe 100 and needle hub 104 in more detail. FIG. 2 is a partial view of the proximal end of the assembled syringe 100 with the needle hub 104 fastened to the barrel 106. FIG. 3 illustrates the assembled syringe 100 with a needle safety shield 114 that is generally disposed over the needle hub 104 to conceal the needle 102 for protective purposes. As illustrated in FIG. 3, the needle hub 104 includes a flange 116 that radially extends beyond the circumferential surface of the barrel 106 and interfaces with the needle safety shield 114, but leaving a circumferential surface of the flange 116 exposed.

As best illustrated in FIG. 2, the needle hub 104 includes a visually coded mark to identify a parameter of the syringe 100. In this exemplary embodiment, the circumferential surface of the flange 116 includes a visually coded mark 118 so that a user may easily identify the syringe 100 when the safety shield 114 is disposed over the needle 102 for protective purposes. For instance, the mark 118 may be a particular color (e.g., black, red, or blue) on the flange 116 to identify the insulin concentration associated with the barrel 106. In other exemplary embodiments, the mark 118 may be selectively applied to any portion of the needle hub 104. For instance, the entire flange 116 may include the mark 118. In other examples, the needle hub 104 may include a logo, text, or any other suitable distinguishing mark on any surface of the needle hub 104. The mark 118 may be used to indicate any suitable characteristic of the syringe including, without limitation, needle gauge, needle length, needle type, barrel radius, barrel volume, medication, and so forth. In other exemplary embodiments, the circumferential surface of the flange 116 having the mark 118 may be planar with the surface of the barrel 106. In yet other embodiments, a circumferential mark on an aspect of the molded barrel could be an equivalent to a mark on the needle hub.

In one exemplary embodiment, the mark 118 may be applied to needle hub 104 by applying an ultraviolet (UV) resin to the surface of the needle hub 104 and exposing the needle hub to UV light. In such an embodiment, the UV resin reacts to the UV light and creates the mark 118. For instance, a suitable UV ink by Capex Corporation may be used due to its polymerization initiated by exposure to the UV light. However, any suitable method of applying a visually coded mark may be used to create the mark 118 such as, without limitation, pad printing, dipping, roll printing, laser treating, two-shot molding, and so forth.

FIG. 4 is a perspective view illustrating the needle hub 104 in more detail. An opening 120 on an end of the needle hub 104 is configured to receive the barrel 106. The opening 120 includes an inner surface having a recessed surface 122 configured to fasten the needle hub 104 to the barrel 106. The needle hub 104 also includes a needle base 124 having shape unique to the manufacturer to distinguish it from competitor's products. In the example of FIG. 4, the base 124 is cylindrical having a radius substantially similar to the radius of the barrel 106 and includes a rounded end that tapers to be planar with and expose the needle 102. As illustrated in FIG. 4, the needle 102 axially extends from the needle base 124. As described above, the needle base 124 is also configured to receive and keep the safety shield 114 in a substantially fixed position.

Figure 5:
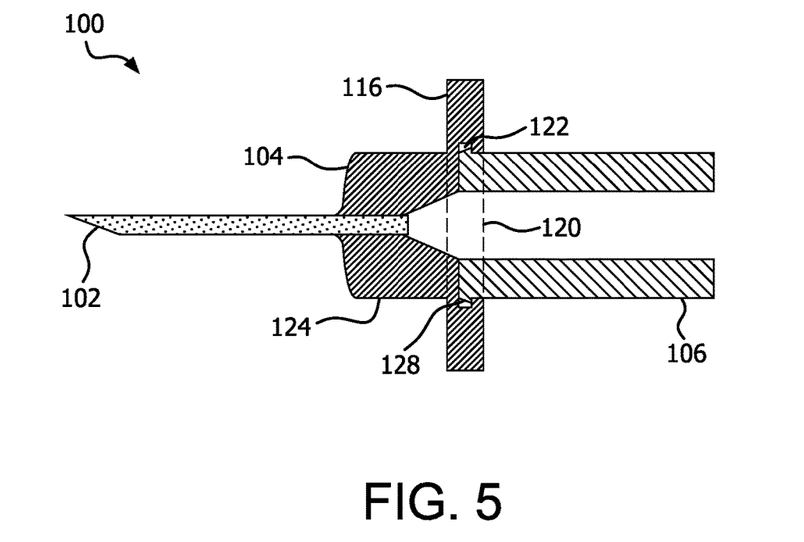
FIG. 5 is a cross-sectional view of the proximal end of the syringe of FIG. 1.

FIG. 5 is a cross-sectional view of the proximal end of the syringe 100 in the axial direction of the needle 102 that illustrates the recessed surface 122 of the opening 120 engages a tapered notch 128 on an outer surface of the barrel 106. In this exemplary embodiment, when the opening 120 of the needle hub 104 axially receives the barrel 106 during assembly, the tapered notch 128 becomes biased by the inner surface of opening 120. When the tapered notch 128 is displaced adjacent to the recessed surface 122, the tapered notch 128 unbiases into the recessed surface 122 to fasten the needle hub 104 to the barrel 106. That is, the recessed surface 122 and the tapered notch 128 implement a latching mechanism to fix the needle hub 104 to the barrel 106. The latching mechanism of the syringe 100 can be formed by any suitable arrangement that keeps the needle hub 104 fastened to the barrel 106 (e.g., a luer lock, etc.). In other examples, the needle hub 104 and the cylinder 106 may be molded as a single device.

Figure 6:
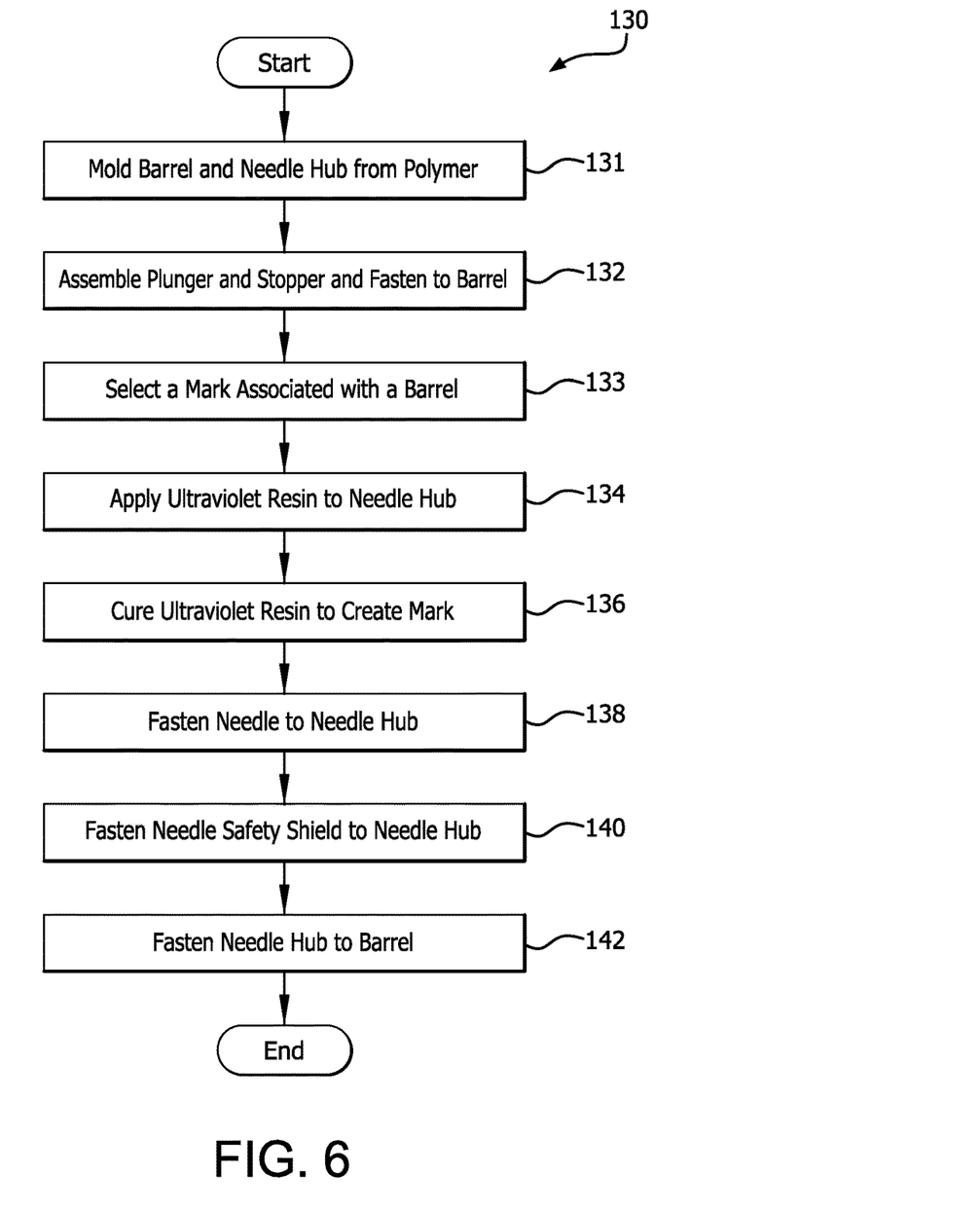
FIG. 6 is a flowchart showing an exemplary process for manufacturing the syringe of FIG. 1.

FIG. 6 illustrates an exemplary process 130 that may be implemented to manufacture the syringe 100. The exemplary process 130 starts by using a polymer to mold a generic barrel and a generic needle hub at step 131. At step 131, any suitable mark may be formed on the surface of the barrel to indicate volume or units of medication. After any marks are formed on the barrel, the stopper and plunger are assembled and placed into the distal opening of the barrel at step 132.

At step 133, a mark is selected for the needle hub associated with the visual marks on the cylindrical barrel. In other exemplary embodiments, the exemplary process 130 may begin by selecting a mark associated with a needle length, needle gauge, or any other syringe characteristic. A UV resin associated with the selected mark is applied to a needle hub corresponding to the barrel at step 134. In one example, the UV resin is applied to the circumferential surface on the flange of the needle hub. In other exemplary embodiments, the UV resin may be applied to the entire needle hub or patterns of UV resin may be selectively applied to any surface of the needle hub as described above. After applying the UV resin to the needle hub, the needle hub is exposed an UV light source to cure the resin and polymerize the resin to the needle hub to create the mark on the needle hub at step 136. In one example, the ultraviolet resin may cause the needle hub flange to be black, red, or blue. However, any color or combination of colors or patterns (e.g., a stripe, a dashed line, etc.) may be used.

After curing the resin, a needle is fastened to the needle hub at step 138 by any suitable means (e.g., epoxy, etc.). The exemplary process 130 continues placing a needle safety shield over the needle hub at step 140. The needle hub is then fastened to the barrel at step 142 by placing barrel 106 into an opening of the needle hub as described above.

The above-described exemplary embodiments allow a generic needle hub to be molded and fitted with any suitable needle, thereby requiring only one generic needle hub for each barrel radius. Further, the mark on the needle hub is always exposed, even with a needle safety shield 114 in place, and provides a visual indicator of the content (e.g., insulin concentration, medication, etc.) or other characteristic of the syringe (needle gauge, needle length, barrel volume, barrel radius, etc.). Because the colored mark on the flange extends from the circumferential surface of the barrel, it can be easily seen from any angle. In other examples, the needle hub may be fabricated with the needle already fixed in place prior to creating the mark with the UV resin. Another exemplary embodiment may further comprise filling the assembled syringe 100 with a medication such as insulin. In such an example, the insulin concentration in the syringe is associated with the colored mark on the syringe. Other exemplary embodiments may further comprise a safety syringe having the mark as described above.

Figure 7:
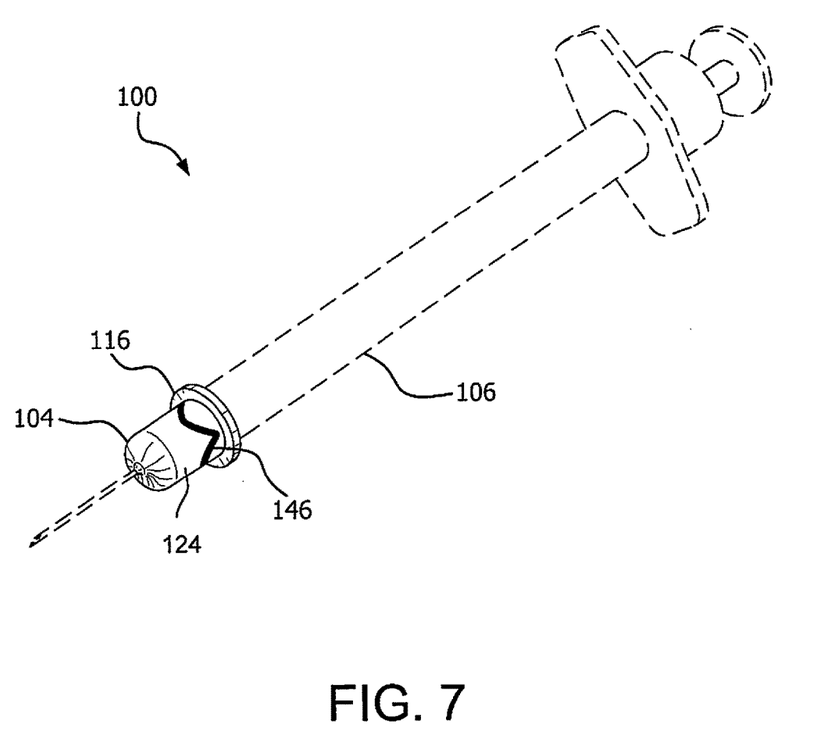
FIG. 7 is a perspective view of another example syringe in accordance with an exemplary embodiment of the present invention.

FIG. 7 illustrates another example of the syringe 100 with the needle hub 104. In the example of FIG. 7, a mark 146 is selectively placed on the circumferential surface of the base 124 and/or flange 116 via laser marking. As an example, the mark 146 is an arcing line around the circumference of the base 124 as illustrated in FIG. 7. Any suitable line, pattern, a sawtooth wave, a sinusoidal line, or a graphic may be implemented such as, for example, a helical line, a logo, and so forth. Further, the needle hub 104 and/or barrel 106 may be selectively laser treated to create a color shade on the needle hub 104 and/or barrel 106 over the entire surface. In other examples, the surface of the needle hub 104 may be selectively treated in a stipple pattern via the laser marking to create a tinted region. For example, the region between the mark 146 and the flange 116 may be selectively treated by the laser to create a shaded region on the needle hub 104. In such an exemplary embodiment, the selective laser treatment may be in black only, or in other colors envisioned. The laser marking affects the surface and sub-surface of the molded plastic, resulting in a more permanent mark without substantial thermal damage to the surface of the syringe. Further, the amount of laser making dye can be altered to alter the color shade.

Figure 8:
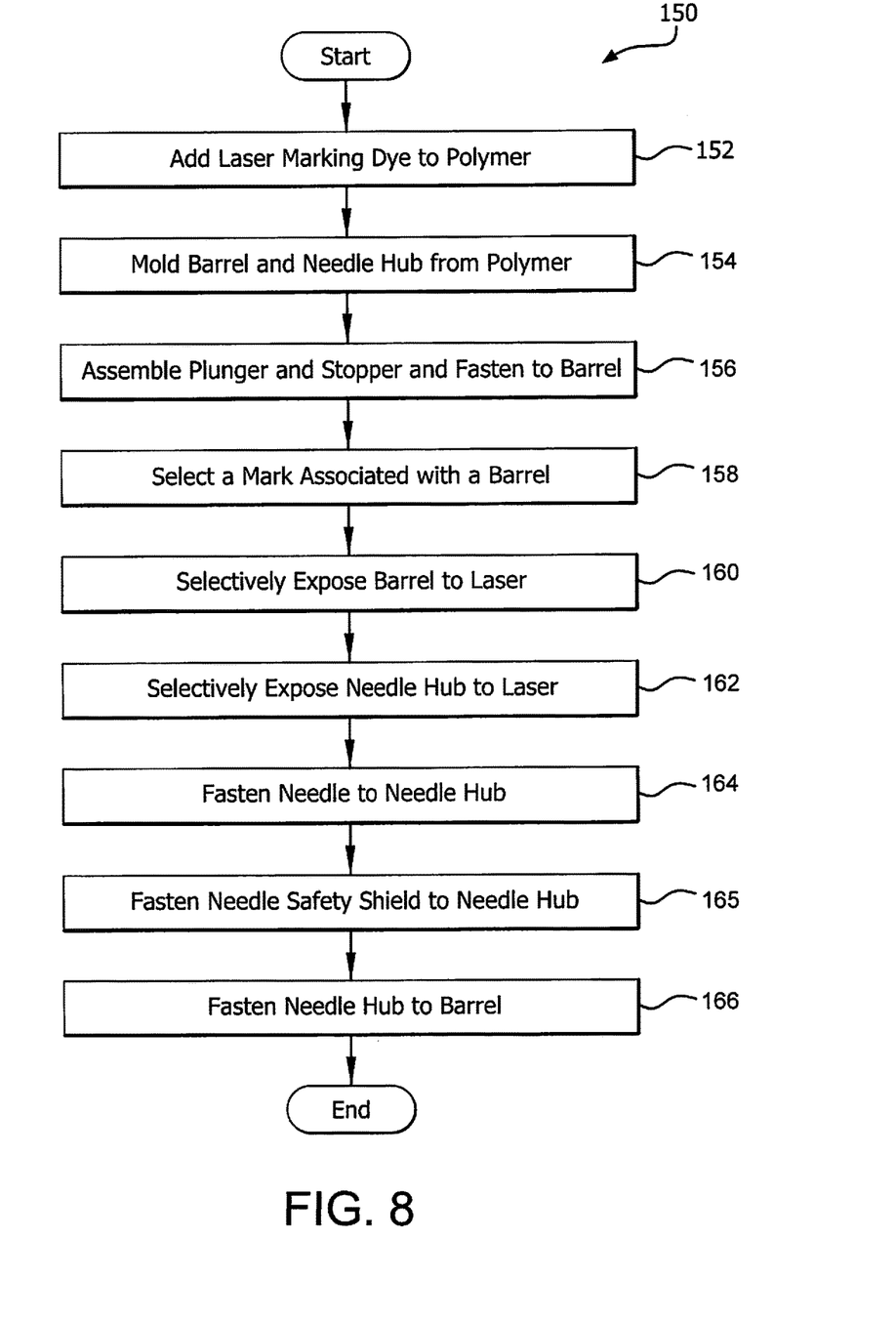
FIG. 8 is a flowchart showing an exemplary process for manufacturing a syringe of FIG. 7.

FIG. 8 illustrates an exemplary process 150 to make the syringe 100 of FIG. 7. At step 152, the exemplary process 150 begins by adding a laser marking dye to a polymer (e.g., polyethylene). One example laser marking dye is an OnCap™ Fast Mark™ laser marking additive, which absorbs the light to generate heat, thereby causing the surface of the polymer to carbonize at the exposed location. The polymer is then used to mold a generic barrel and a generic needle hub at step 154. At step 154, any suitable mark may be formed on the surface of the barrel to indicate volume or units of medication. The stopper and plunger are assembled and placed into the distal opening of the barrel at step 156

The barrel is then selectively exposed to a laser source, which reacts with the laser marking dye to create a mark at step 158. At step 158, to prevent substantial damage to the plastic of the barrel, the laser source selectively exposes portions of the surface of the barrel at fine intervals to create a color shade on a region of the barrel without creating substantial thermal damage on its surface. The needle hub is then selectively exposed to the laser source to create a fine pattern to create a color shaded on its surface at step 160. In the exemplary process 150 at step 162, the needle hub may also be selectively exposed to create a solid line, a pattern, a logo, or other text at step 162 (e.g., an arcing line similar to the mark 146).

After laser marking the needle hub and/or barrel, the needle is fastened to the needle hub at step 164 by any suitable means (e.g., epoxy, etc.). A needle safety shield is placed over the needle and needle hub at step 165. The needle hub is fastened to the barrel at step 166 by, for example, placing the barrel into the opening of the needle hub and then applying a force to cause the fastener to latch to the barrel as described above.

The above-described examples allow a selectively color shaded needle hub with a mark and/or a shaded barrel. The shaded barrel and/or shaded needle hub can be used in conjunction to identify multiple syringe characteristics. For instance, the needle hubs may have no shade if the needle length is less than 6 millimeters (mm) and a light shade if greater 6 mm. In such an example, the flange of the needle hub may be marked with a color by a UV cure process as described above to indicate additional syringe characteristics. In other examples, the shade of the needle hub, the shade of the barrel, a color mark on the base, and a color mark on the flange may be a visual indicator of the content (e.g., insulin concentration, medication) and/or other parameters of the syringe (needle gauge, needle length, barrel volume, barrel radius, etc.). The shade of the mark can be adjusted by, for example, adjusting the amount of laser marking dye added to the polymer.

Figure 9:
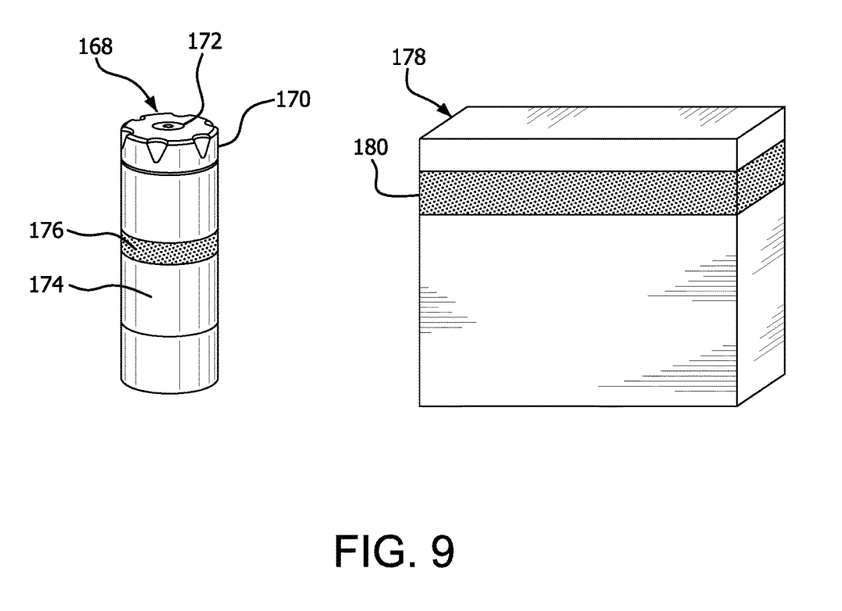
FIG. 9 illustrates an insulin storage container and a retail packaging according to an exemplary embodiment of the present invention.

The color of the mark 118 may also be disposed on additional materials that are associated with the syringe 100 for a user's convenience. For instance, as illustrated in FIG. 9, an insulin container 168 may include a cap 170 having a substantially similar color to the mark 118. In such an example, the syringe 100 pierces a septum 172 disposed on the cap to withdraw insulin from the insulin storage container 168 into the syringe 100. The insulin container 168 may also have a label 174 having a display visual indicator 176 having a substantially identical color of the mark 118 so that the user can easily identify the correct syringe. The substantially matching colors of the mark 118 on the syringe 100, the cap 170, and the label 174 provide a visual indication to the user that he or she is withdrawing the correct insulin to be used in the syringe 100. In yet another exemplary embodiment, several syringes 100 may be pre-filled with the insulin and provided to the user in a retail package 178. In such an embodiment, an exterior surface of the package may display visual indicator 180 having a substantially identical color of the mark 118 so that the user can easily identify the correct syringe.

In each of the embodiments disclosed herein and in other alternative embodiments, the syringe molded components can be made of polypropylene, polyethylene, polyethylene terephthalate, and/or bio-derived resins such as polylactide, starch-filled polypropylene, or polyhydroxyalkanoates. Alternatively, bio-degradable resins may be used to form the syringe molded components. The needle on the needle hub can be fixed to the needle hub either before or after the marking is placed on the needle hub. As described above, when provided to the user, the syringe can be filled with medication (e.g., insulin) or may be empty so a user can withdraw the medication from a corresponding container. The user may retrieve the syringe from packaging that is also marked with the substantially identical color, thereby providing the user multiple notifications as to the insulin concentration that will be injected. This ensures the user will use the correct amount of insulin by implementing multiple warnings using a visual indicator such as a particular color, pattern, and so forth.

Although only a few exemplary embodiments of the present invention have been described in detail above, those skilled in the art will readily appreciate that many modifications are possible in the exemplary embodiments without materially departing from the novel teachings and advantages of this invention. Accordingly, all such modifications are intended to be included within the scope of the appended claims and their equivalents.

What is claimed is:

1. A method of assembling a medication delivery device, comprising: forming a barrel;
    forming a needle hub, selecting a colored mark to place on an outer surface of the needle hub, and creating the colored mark on the outer surface so that it extends substantially around an entire circumference of the needle hub;
    attaching a needle to the needle hub; and
    attaching the needle hub to the barrel;
    wherein the colored mark corresponds to a characteristic of the medication delivery device or its content; and wherein forming the barrel and the needle hub comprises selecting a polymer and adding a laser sensitive dye to the polymer for forming the barrel and the needle hub, and wherein the laser sensitive dye is selected based on the colored mark to be created on the needle hub.

2. The method as recited in claim 1, wherein creating the colored mark on the outer surface of the needle hub comprises applying an ultraviolet sensitive resin to the needle hub and exposing the resin to an ultraviolet light.

3. The method as recited in claim 1, further comprising selectively exposing one of the barrel and needle hub to a laser source to selectively activate the laser sensitive dye to create a color on a respective surface.

4. The method as recited in claim 1, wherein forming the needle hub comprises forming the needle hub to have a flange.

5. The method as recited in claim 4, further comprising exposing the needle hub to a laser source to create the colored mark on one of a flange and a base of the needle hub.

6. The method as recited in claim 1, wherein the colored mark is substantially identical to a color of a cap or label on an insulin container for withdrawing insulin therefrom by operation of the medication delivery device.

7. The method as recited in claim 1, further comprising packaging the medication delivery device into a container having an exterior surface, wherein the surface features a mark that has a color substantially identical to the colored mark on the needle hub.

8. The method as recited in claim 1, wherein forming the barrel further comprises selecting visual marks to place on the barrel, and creating the selected visual marks on a surface of the barrel.

9. The method as recited in claim 8, wherein the colored mark is associated with visual marks on the surface of the barrel.

\* \* \* \* \*

UNITED STATES PATENT AND TRADEMARK OFFICE
CERTIFICATE OF CORRECTION

PATENT NO. : 10,130,769 B2
APPLICATION NO. : 15/012687
DATED : November 20, 2018
INVENTOR(S) : Amit Limaye et al.

It is certified that error appears in the above-identified patent and that said Letters Patent is hereby corrected as shown below:

In the Claims

Column 7, Line 19, delete "a" (first occurrence) and insert -- the -- therefor.

Signed and Sealed this
Nineteenth Day of February, 2019

Andrei Iancu
*Director of the United States Patent and Trademark Office*